United States Patent [19]

Jalinous

[11] Patent Number: 5,718,662
[45] Date of Patent: Feb. 17, 1998

[54] APPARATUS FOR THE MAGNETIC STIMULATION OF CELLS OR TISSUE

[76] Inventor: Reza Jalinous, 22 Maes-y-felin, Fforestfach, Swansea, United Kingdom, SA5 5DW

[21] Appl. No.: 532,612

[22] PCT Filed: Feb. 10, 1995

[86] PCT No.: PCT/GB95/00262

§ 371 Date: Dec. 14, 1995

§ 102(e) Date: Dec. 14, 1995

[87] PCT Pub. No.: WO95/21655

PCT Pub. Date: Aug. 17, 1995

[30] Foreign Application Priority Data

Feb. 10, 1994 [GB] United Kingdom .................. 9402545

[51] Int. Cl.$^6$ .................................................. A61N 1/00
[52] U.S. Cl. ............................................. 600/13; 128/897

[58] Field of Search ...................... 600/9–15; 128/897–98

[56] References Cited

FOREIGN PATENT DOCUMENTS

| | | |
|---|---|---|
| 0271174 | 6/1988 | European Pat. Off. . |
| 1401682 | 10/1965 | France . |
| 2676930 | 12/1992 | France . |
| A3244582 | 12/1984 | Germany . |
| 2261820 | 6/1993 | United Kingdom . |

Primary Examiner—John P. Lacyk
Attorney, Agent, or Firm—Nixon & Vanderhye P.C.

[57] ABSTRACT

A stimulator for neuro-muscular tissue having a stimulating coil which is energized by discharging capacitors at different times in parallel connected discharge circuits so as to provide amplitude and/or frequency modulation of the stimulating pulses.

3 Claims, 2 Drawing Sheets

APPARATUS FOR THE MAGNETIC STIMULATION OF CELLS OR TISSUE

This invention relates to apparatus for magnetically stimulating neurones and in particular neuro-muscular tissue by inducing therein electric current using time varying magnetic fields, and for similar purposes such as the stimulation of cells in cell cultures. Broadly, the invention concerns a magnetic stimulator which is capable of producing pulse trains of which both frequency and amplitude are controllably variable and particularly concerns a stimulator comprising a multiplicity of capacitor discharge units of which the outputs can be coupled in parallel.

In a preferred form of the invention, a multiplicity of discharge units, each of which is capable of independent operation and is disposed to provide an output in parallel with the output of one or more other units so as to provide various outputs such as pulses of greater power or pulse strains of different frequency. Each unit may be coupled to a charging circuit and may include at least one pulse forming capacitor and a controllable discharge circuit.

The various units may be supervised by an electronic control circuit which may itself be controllable by means of a remote controller.

In a preferred form of the invention, the outputs from the discharge units maybe combined and fed to an output so that, for example, two of the units may provide outputs which can be coupled to a first output terminal and two or more further units may provide an output which can be coupled to a second output terminal. This arrangement enables the use of either one or two stimulating coils with independent pulsing control. It also provides for a certain fault tolerance, so that if one or two units failed it would still be possible to utilize one of the outputs of the circuit.

The stimulating power of each unit can be controlled by varying the energy initially installed in the unit by variation of the stored capacitor voltage. Thus a multiplicity of different amplitudes can be selected, one for each of the plurality of magnetic stimulator units for each pulse train thereby to provide amplitude variation or modulation of the pulse train. Random variation could also be employed.

The use of a multiplicity of units in parallel enables the spacing between successive stimulating pulses to be very short, even zero. Frequency modulation can be provided by variation of the interpulse spacing.

The combined outputs from a multiplicity of units may also be such as to increase output power by simultaneous or nearly simultaneous multi-channel discharge.

Each unit may typically recharge in a cycle which lasts approximately two to four seconds depending on the power level, stored energy and charging rate. It is feasible to increase the discharge repetition rate by at least a factor of N where N is the number of capacitors, by discharging all the capacitors in a time sequence. Thus at lower power levels and for a two second recharge time, a 4 Hz discharge repetition rate is possible for an eight capacitor system. More versatile systems containing additional capacitors enabling a wider range of amplitude and frequency variation can be envisaged.

DETAILED DESCRIPTION OF PREFERRED EMBODIMENTS

Figure 1:
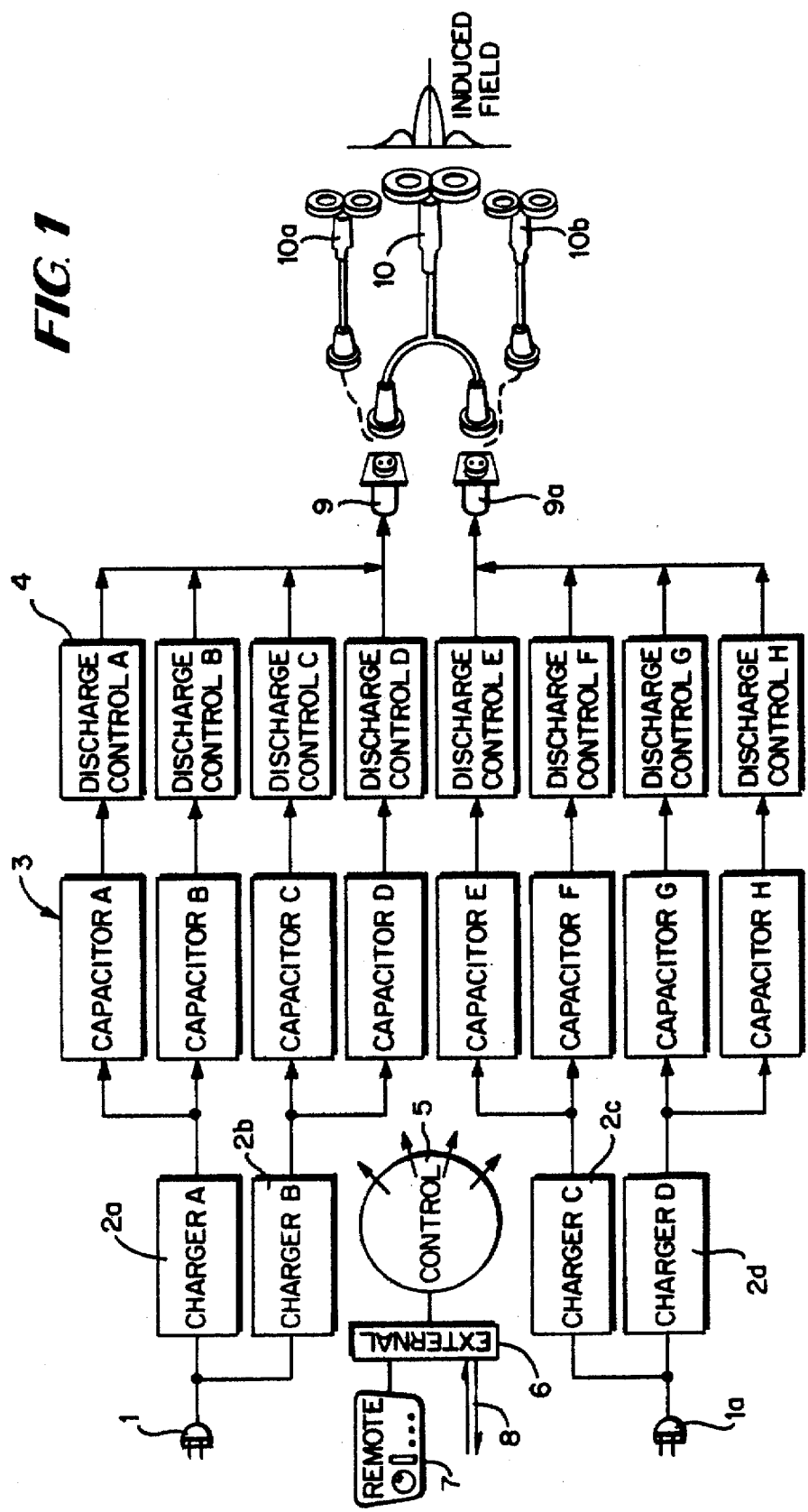
FIG. 1 is a schematic representation of a magnetic stimulator according to the invention.

FIG. 1 illustrates an apparatus for providing magnetic stimulation of neuro-muscular tissues by the application of time varying magnetic fields produced by the application of a multiplicity of capacitor discharge pulses to a stimulating coil, which may be, for example, specially shaped to fit the cranium of a patient. For example, the coil maybe in the form described in our published British Patent Application GB-A-2261820.

In the illustrated system, the apparatus comprises two sets of capacitors 3 each having a respective, independently controllable discharge control, connected in parallel to provide one common output for each set of capacitors. The two outputs maybe used to drive different coils or maybe coupled in parallel to drive a single stimulating coil thereby to extend the range of variation of amplitude or frequency of the pulse trains which can drive the stimulating coil.

A mains power input terminal 1 is coupled to provide alternating current to two chargers 2a and 2b. Each of these chargers may comprise, in any desired circuit configuration, a transformer rectifier circuit and some means of controlling output voltage. Such circuits are well known to those skilled in the art and will not be described in detail.

Each charger could be connected to charge a respective capacitor but for preference in the present embodiment each of the two chargers charges a respective pair of the capacitors 3, the charger 2a being connected to charge capacitor A and capacitor B and charger 2b being connected to charge capacitor C and capacitor D.

In like manner, a second power input 1a provides power to two chargers 2c and 2d respectively, the charger 2c being connected to charge capacitor E and capacitor F and charger 2d being connected to charge capacitor G and capacitor H.

Thus the capacitors may by virtue of the control by the chargers 2a to 2d be charged with a variety of charges but for simplicity it will be supposed that the various capacitors are of the same capacitance and store the same charge.

Each of the capacitors is provided with a respective discharge control 4. The discharge controls are controllable at independently selectable times by means of a controller 5, which by means of an interface 6 may be controlled remotely by means of a remote control unit 7 or locally by means of a trigger input 8. The controller 5 may be of any desired construction, it being sufficient for the purposes of the present invention that the controller 5 can provide eight switching signals at independently controllable times, for operation of the discharge controls 4. The controller 5 may include a microprocessor or may be controlled using a suitable interface from the output of a computer.

The output terminals 9 and 9a, one for each set of capacitors, may be coupled in parallel to drive a single stimulating coil 10 or be connected separately to respective stimulating coils 10a and 10b.

According to the timing of the discharge control signals available from the controller 5, the pulse outputs may be combined so as to provide one or more pulses of variable amplitude and spacing. For example, four capacitors may be discharged at evenly spaced times to provide a train of four pulses. Two pairs of capacitors may be discharged at respective times to provide a pulse pair of higher amplitude or a multiplicity of capacitors may be discharged simultaneously to provide a single pulse.

The cycle of control of discharge may be repetitive and the pulse timing can be adjusted within each cycle so as to provide a substantially continuous stream of pulses exhibiting either frequency modulation amplitude modulation or a combination of both frequency and amplitude modulation.

Figure 2:
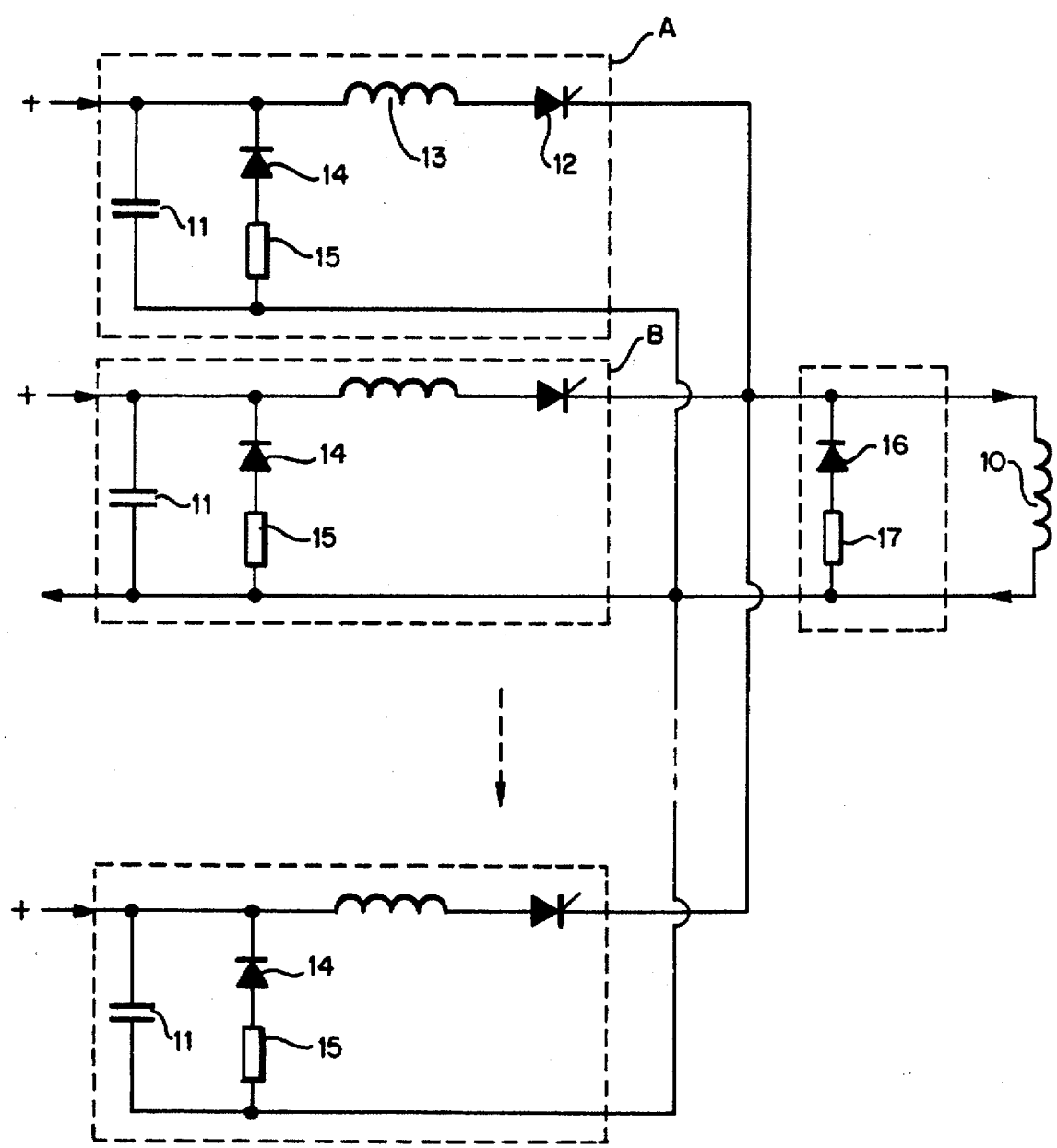
FIG. 2 is a more detailed schematic diagram of part of a stimulator according to the invention.

FIG. 2 illustrates a detailed schematic of several capacitors 11 etc corresponding to the capacitors A, B etc in FIG.

1. Each capacitor forms a module with an associated discharge control. Each of the discharge units (modules) A, B in FIG. 2 is capable of providing a stimulating pulse in the coil 10 of which only one needs description. The modules A, B etc maybe all the same. In this embodiment a storage capacitor 11 is discharged by means of a series switch 12 which is controllable by means of control signals from the controller (not shown in FIG. 2) and is preferably but not essentially constituted by a controlled rectifier such as a thyristor. In series with the capacitor 11 and switch 12 is a current limiter which may be an inductor 13. The output port of each discharge unit is connected in parallel with the other output ports of the other discharge units and the common output lines are shown as connected to a stimulating coil 10.

Only the operation of a single discharge control circuit need be described in detail.

The switch 12 of the first channel is normally open, i.e. non-conductive, the capacitor 11 being charged by a respective charger to a desired voltage. In parallel with the capacitor may be a branch containing a diode 14 and a resistor 15. The diode is reverse-biased when the capacitor 11 is charged.

At the desired time the switch 12 is rendered conductive by a control signal at its gate. The discharge current from the capacitor flows through the stimulating coil 10. As energy is tranferred from the capacitor to the stimulating coil the voltage across the capacitor diminishes and eventually reverses polarity. At this point the diode becomes forward-biased and begins to conduct. The discharge current falls until it reaches zero. The switch 12 maybe made non-conductive at this time.

The diode 14 and resistor 15 act to limit the voltage reversal. For small values of the resistor 15 the voltage reversal is clamped to a low value. If desired, the diode 14 or the resistor 15 or both maybe omitted. The various circuit configurations determine the shape of the waveform obtained.

Inductor 13 is employed to limit the rate of change of current and ultimately control the-peak discharge current in the case of a short circuited output. The use of an inductor is quite useful because it enables an inherently parallel system with short circuit protection. In some cases, owing to the of the spurious inductance possessed by all wiring and components, the total spurious inductance may be sufficient to provide short circuit protection.

The switch 12 is preferably a thyristor but other switching devices such as thyratrons, triacs, transistors and relays might be used. Controllable switches, particularly controllable rectifiers may be used in place of the diodes 14.

If desired, a reverse diode 16 in series with a resistor 17 may comprise a branch in parallel with the coil 10; these components have the same purpose as the diodes 14 and resistors 15.

I claim:

1. A stimulator circuit for providing a pulse output for a stimulating coil for the stimulation of cells or tissues by means of a time varying magnetic field produced by said stimulating coil in response to said pulse output, said stimulator circuit comprising:

a plurality of discharge channels, each channel comprising a respective charge storage capacitor and electrically controllable means for discharging said respective capacitor;

means for coupling said discharge channels in parallel to said stimulating coil so as to couple said pulse output thereto; and means for controlling said electrically controllable means of said channels so as to control the timing of the discharging of the capacitors in said channels whereby to provide amplitude or frequency modulation of said pulse output.

2. A stimulator circuit according to claim 1 in which each channel comprises the respective capacitor, a controllable rectifier and a current limiting inductor in series with the capacitor and a circuit branch including a reverse diode and a resistor in parallel with the capacitor.

3. A stimulator circuit according to claim 1 comprising a further plurality of discharge channels each including a respective storage capacitor and electrically controllable means for discharging said respective capacitor for producing a pulse output for a further stimulating coil, said means for coupling providing coupling of said further plurality of discharge channels to said further stimulating coil and said means for controlling providing control to the electrically controllable means of said further plurality of discharge channels so as to control the timing of the discharging of the capacitors of said further plurality of discharge channels.

* * * * *